United States Patent

Oehy et al.

[11] Patent Number: 5,609,648
[45] Date of Patent: Mar. 11, 1997

[54] ACETABULAR CUP ASSEMBLY

[75] Inventors: Jürg Oehy; Kurt Bider, Winterthur; Martin Schoch, Stallikon, all of Switzerland

[73] Assignee: Sulzer Medizinaltechnik AG, Winterthur, Switzerland

[21] Appl. No.: 379,836

[22] Filed: Jan. 27, 1995

[30] Foreign Application Priority Data

Feb. 7, 1994 [EP] European Pat. Off. ............... 94810064

[51] Int. Cl.⁶ ........................................... A61F 2/32
[52] U.S. Cl. ................................. 623/22; 623/18
[58] Field of Search .................. 623/16, 18, 19, 623/20, 22, 23; 606/72, 71, 73

[56] References Cited

U.S. PATENT DOCUMENTS

| 4,211,325 | 7/1980 | Wright | 623/2 |
| 4,955,325 | 9/1990 | Zarnowski | |
| 5,021,062 | 6/1991 | Adrey | |
| 5,360,452 | 11/1994 | Engelhardt | 623/22 |

FOREIGN PATENT DOCUMENTS

| 0313762 | 5/1989 | European Pat. Off. | |
| 0346270 | 12/1989 | European Pat. Off. | 623/22 |
| 0444381 | 9/1991 | European Pat. Off. | |
| 0472315 | 2/1992 | European Pat. Off. | |
| 0490616 | 6/1992 | European Pat. Off. | |
| 2668055 | 4/1992 | France | |

Primary Examiner—David Isabella
Attorney, Agent, or Firm—Townsend and Townsend and Crew LLP; J. Georg Seka; John T. Raffle

[57] ABSTRACT

A joint socket (2) for a hip joint prosthesis comprises an outer shell (5) adapted for being anchored into a bone seat and an inner shell (6) adapted for receiving a ball of a joint. A threaded plug (10) is threadably coupled within a threaded bore (8) of the outer shell and a projection (22) extends from the polar region of the inner shell into an axial recess (20) of the threaded plug for centering the inner shell relative to the outer shell. The threaded plug seals off the inner volume of the outer shell, thereby preventing contact between rubbed off particles of the interacting inner and outer shells and the bone tissue. In addition, it allows the surgeon to directly observe the bone tissue lying behind the threaded bore of the implanted outer shell.

8 Claims, 1 Drawing Sheet

ACETABULAR CUP ASSEMBLY

The invention relates to a joint socket of a hip joint prosthesis having at least two-shells: an outer shell anchored into the bone seat and an inner shell for receiving the ball of a joint.

The invention further relates to a hip joint prosthesis provided with a joint socket of this kind and also to a threaded plug for a joint socket of this kind.

BACKGROUND OF THE INVENTION

A joint socket of the named kind is described in U.S. Pat. No. 5,021,062. A threaded bore provided in the pole region of the outer shell of the known joint socket is intended to simplify the positioning of the outer shell in the bone tissue and to provide the surgeon with a provisional fixation of the outer shell in the bone tissue, for instance by means of a holder which can be. In addition, the threaded bore can serve as a guide bore for a centering part which projects from the inner shell made of plastic. In joint sockets of this kind, rubbed-off particles may be produced under loading, for instance, due to elastic deformation of the interacting parts. These particles can escape into the part of the bone seat adjacent to the threaded bore situated between the wall of the threaded bore and the centering part moveably guided therein.

SUMMARY OF THE INVENTION

The object of the invention is to provide an improved joint socket which prevents the escape of rubbed-off particles produced by wear into the bone tissue surrounding the outer shell.

The present invention comprises a joint socket for a hip joint prosthesis comprising an outer shell adapted for being anchored into a bone seat and an inner shell adapted for receiving a ball of a joint. The outer shell includes a perforated threaded bore for receiving a driver tool. A threaded plug is threadably coupled within the threaded bore of the outer shell for sealing the threaded bore from the bone seat. A projection extends from the inner shell and has a center portion projecting into an axial recess of the threaded plug. The projection allows the inner shell to be precisely positioned within the outer shell. The threaded plug seals off the inner volume of the outer shell, thereby preventing contact between rubbed off particles of the interacting inner and outer shells and the bone tissues. In addition, it allows the surgeon to directly observe the bone tissue lying behind the threaded bore of the implanted outer shell.

A reliable sealing off of the inner volume of the outer shell from the bone seat is achieved in a simple manner by the embodiment of the hip joint in accordance with the invention. Correspondingly, a contact between any rubbed-off particles which may be present and the bone tissue is prevented and thereby the danger of a further spread of such rubbed-off particles avoided (e.g., a transmission into the blood stream). The embodiment of the inventiong also permits the formation of an observation location which is free from outside influences and which makes a checking of the condition of the part of the bone seat lying under the outer shell possible without having to remove the outer shell from the bone seat.

BRIEF DESCRIPTION OF THE DRAWINGS

The invention is described with the aid of embodiments which are schematically illustrated in the drawing. They show.

DESCRIPTION OF THE PREFERRED EMBODIMENTS

Figure 1:
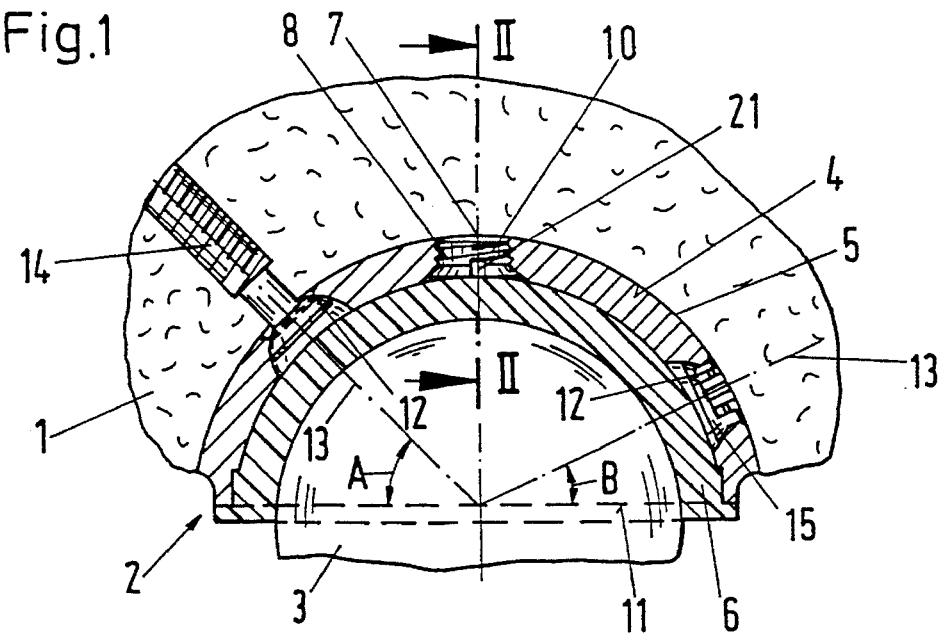
FIG. 1 parts of a hip joint prosthesis comprising a hip joint formed in accordance with the invention and in a diametrically extending section.
Figure 2:
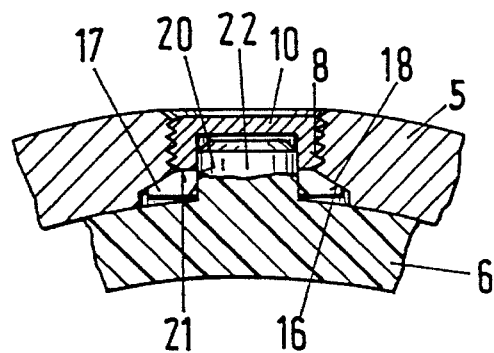
FIG. 2 a detail of the hip joint in an enlarged scale in a section corresponding to the line II—II in FIG. 1.
Figure 5:
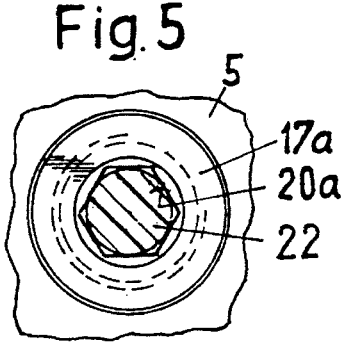
FIG. 5 is a top sectional view of a polygonal socket taken along lines V—V in FIG. 3.

The hip joint prosthesis of FIGS. 1 and 2 comprises a joint socket 2 which is fittable into the bone tissue 1 of a human pelvis and a joint head 3 which is fastenable in a femur via a shank part which is not illustrated. The joint socket 2 comprises a metallic outer shell 5, for example made from titanium, which is insertable into and anchorable in a prepared bone seat 4 and which is substantially in the form of a hollow hemispherical and a matched inner shell 6 which can be fitted therein and which is also hemi-spherical and which receives the joint head 3 and which, in accordance with the illustration, is made from a plastic such as polyethylene. In accordance with another embodiment, a corresponding metallic inner shell can also be provided. In accordance with a further embodiment which is not illustrated, there may also be provided an intermediate shell between the outer shell 5 and the inner shell 6, wherein the intermediate shell can be made from a plastic or a metal.

In the region of its pole 7, the outer shell is provided with a perforating, radial threaded bore 8 intended for the receipt of a driver tool which can be screwed into it from the inside outwards for the positioning of the outer shell 5 and also the receipt of a corresponding threaded plug 10 and which allows a control of the penetration depth of the outer shell 5 in each case. Further radial bores 12 which are displaced relative to one another in the circumferential direction are provided between the pole 7 and the equator 11 of the outer shell 5, which traverse the outer shell with axes 13 inclined in various angles A and B relative to the plane of the equator 11. The bores 12 are each provided for the receipt of a fastening element 14 of any kind which is anchorable in the bone tissue 1, in accordance with the representation in the form of a bone screw is capable of being screwed into the bone tissue 1. Two or more, preferably three corresponding fastening elements 14 can be provided for the fastening of the outer shell 5 in the bone seat 4. The bores 12 which have not been utilized and are free of fastening elements 14 can each be provided with a closure element 15 which is insertable into and fastenable from the inside of the bore outwards, this element not being subject matter of the current invention.

Corresponding to the illustration of FIGS. 1 and 2, the threaded bore 8 is provided with a conical counter-sink 16. The threaded plug 10 is provided with a flange part 17 which can be fitted flush into this counter-sink 16, and at which a corresponding press shoulder 18 placeable onto the counter-sink 16 is formed. The threaded plug 10 is further provided with a recess 20 which is open towards the inner shell 6 as well as with contact surfaces for a screw driving tool (not illustrated) which are formed on the slit 21 traversing the flange part 17. The recess 20 is, in accordance with FIG. 2, formed by a central blind bore which is provided for the receipt of a spigot-like projection 22 which protrudes from the inner shell 6 and which can be centered in the recess 20. A screw driver insertable into the slit 21 can be provided as the screw driving tool, via which the threaded spigot 10 can be screwed into and removed from the threaded bore 8. Correspondingly, on the one hand, an effective sealing off of the threaded bore 8 can be achieved in a simple manner and thereby the escape of rubbed-off particles which may form inside the hip joint into the bone tissue can be reliably prevented; on the other hand the section of the bone seat 4 lying in the region of the threaded bore 8 is, when the inner shell 6 has been removed, accessible at any time for determining check of the condition of the bone tissue 1. If the bone tissue 1 is unchanged or intact, removal of the outer shell 5 can be omitted if desired and merely a new inner shell 6 or a corresponding intermediate shell fitted into the outer shell 5, centered by the threaded bore 8 and fitted together with a new, or alternatively the existing ball of the joint 3.

Figure 3:
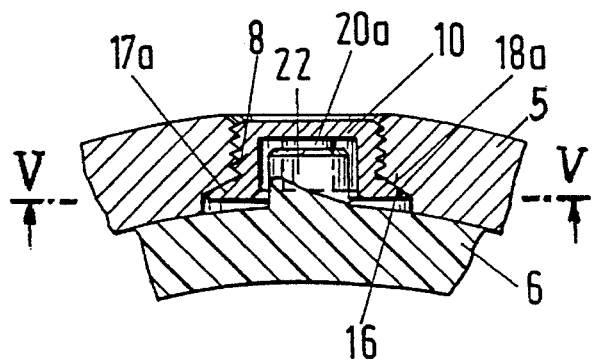
FIGS. 3 and 4 further details of hip-joints each in a representation corresponding to that of FIG. 2 and each in a derivative embodiment.
Figure 6:
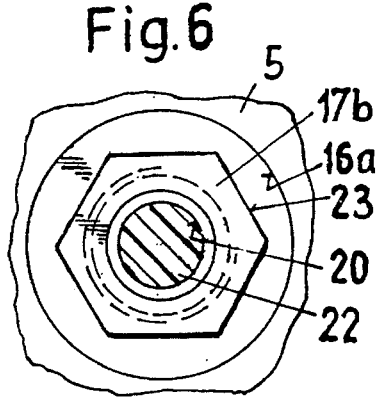
FIG. 6 is a top sectional view of a polygonal head taken along lines VI—VI in FIG. 4.

In the embodiment of FIG. 3, the threaded plug 10 is provided with a recess 20a which has a cross-section in the form of a polygonal socket, in the figure a hexagonal socket, and wherein the contact surfaces for the screw driving tool, which is insertable as an Allan key, is formed by the corresponding surfaces of the concave polygon. In this embodiment, a flange part 17a can be provided with a conical sealing surface 18a extending around the circumference of the counter-sink 16, via which a correspondingly improved sealing off of the threaded bore 8 against the inner side of the outer shell 5 is achievable. The described arrangement of the flange part 17a, whereby it is fittable flush in the counter-sink 15 of the threaded bore 8, necessitates an advantageously slight reduction of the wall thickness of the outer shell 5 so that a thread length sufficient for a reliable screw connection can even be obtained for the relatively small wall thicknesses of, for example 3 to 4 mm, such implants. As can further be seen from FIG. 3, the projection 22 of the inner shell 6 can be designed with a diameter which corresponds to the diameter of the circle described by the concave polygon so that the projection 22 can be centered via the surfaces of the concave polygon.

Figure 4:
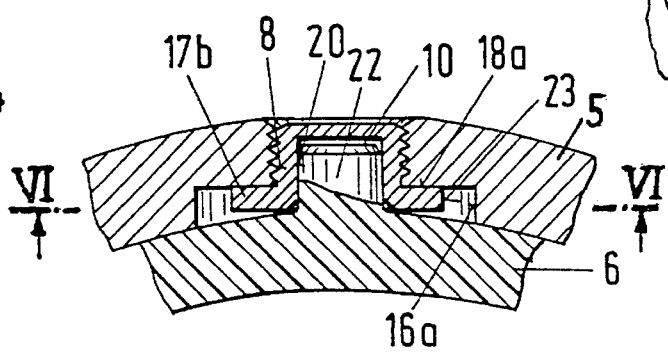

In accordance with FIG. 4, the threaded plug 10 may include a flange 17b which is bounded by contact surfaces 23 in the form of a polygonal head, in particular a hexagonal head. Correspondingly, the threaded plug 10 is adjustable via a spanner or socket which can be applied to these contact surfaces 23 and wherein the threaded bore 8 can be provided with a counter-sink 16a which permits the insertion of a socket (Allan key) insertable into the flange part 17b.

In summary, the invention can be described as follows:

The joint socket 2 comprises an outer shell 5 which is anchorable in a bone seat 4 and an inner shell 6 for the receipt of a ball of a joint 3. In its pole region, the outer shell is provided with a threaded bore 8 which serves for the receipt of a driver tool provided for the positioning of the outer shell 5 and which permits a checking of the part of the bone seat 4 situated thereunder. The threaded bore 8 is sealable from the bone seat 4 via a threaded plug 10 whereby escape of rubbed-off particles produced as a result of wear between the outer shell 5 and the inner shell 6 into the bone tissue 1 is prevented. The threaded plug 10 can be provided with a recess 20 which is open towards the inner shell 6 and in which a spigot-like projection 22 projecting from the inner shell 6 can be centered.

We claim:

1. A joint socket of a hip joint prosthesis comprising:
   an outer shell adapted for being anchored into a bone seat, the outer shell having a perforated threaded bore for receiving a driver tool;
   an inner shell adapted for receiving a ball of a joint, the inner shell having a polar region and an equatorial region;
   a threaded plug threadably coupled within the threaded bore for sealing the threaded bore from the bone seat, the threaded plug having an axial recess opening towards the inner shell; and
   a projection extending from the polar region of the inner shell and having a center portion projecting into the axial recess of the threaded plug to center the inner shell relative to the outer shell.

2. The joint socket of claim 1 wherein the threaded plug defines contact surfaces for receiving a screw driving tool.

3. The joint socket of claim 2 wherein the contact surfaces are formed on a slit traversing the threaded plug and opens towards the inner shell.

4. The joint socket of claim 3 wherein the recess includes partial surfaces arranged in the form of a polygonal socket and the projection comprises a spigot centered within the partial surfaces of the polygonal socket.

5. The joint socket of claim 2 wherein the threaded plug includes partial surfaces arranged in the form of a polygonal head.

6. The joint socket of claim 1 wherein the threaded plug has a press shoulder with a sealing surface seated onto the outer shell, the sealing surface sealing the threaded bore from an inner side of the outer shell.

7. The joint socket of claim 6 wherein the threaded bore includes a counter-sink and the threaded plug has a portion flush with the counter-sink, the sealing surface of the threaded plug being formed at said portion of the press shoulder.

8. A hip joint prosthesis comprising:
   a joint having a ball; and
   a joint socket comprising:
      an outer shell adapted for being anchored into a bone seat, the outer shell defining a polar region and a equatorial region and having a perforated threaded bore for receiving a driver tool;
      an inner shell receiving the ball of the joint;
      a threaded plug threadably coupled within the threaded bore for sealing the threaded bore from the bone seat, the threaded plug having an axial recess opening towards the inner shell; and
      a projection extending from the polar region of the inner shell and having a center portion projecting into the axial recess of the threaded plug to center the inner shell relative to the outer shell.

* * * * *